(12) United States Patent
Kim et al.

(10) Patent No.: US 12,060,326 B2
(45) Date of Patent: Aug. 13, 2024

(54) LAUROLACTAM PREPARATION METHOD AND SYNTHESIS APPARATUS

(71) Applicant: HANWHA SOLUTIONS CORPORATION, Seoul (KR)

(72) Inventors: Jiyeon Kim, Daejeon (KR); Youngjin Kim, Daejeon (KR); Jeongseok Park, Daejeon (KR); Jinho Park, Daejeon (KR); Hyun Seo, Daejeon (KR); Seonghoon Hyeong, Daejeon (KR); Kyuho Song, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 176 days.

(21) Appl. No.: 18/054,558

(22) Filed: Nov. 11, 2022

(65) Prior Publication Data

US 2023/0073615 A1    Mar. 9, 2023

Related U.S. Application Data

(62) Division of application No. 17/311,353, filed as application No. PCT/KR2019/017935 on Dec. 18, 2019, now Pat. No. 11,535,591.

(30) Foreign Application Priority Data

Dec. 19, 2018  (KR) .............................. 102180165237

(51) Int. Cl.
C07D 201/04       (2006.01)

(52) U.S. Cl.
CPC .................................. C07D 201/04 (2013.01)

(58) Field of Classification Search
CPC .................................................... C07D 201/04
See application file for complete search history.

(56) References Cited

U.S. PATENT DOCUMENTS

| 9,533,932 B2 * | 1/2017 | Micoine | ............... C07D 301/12 |
| 11,535,591 B2 * | 12/2022 | Kim | ..................... C07D 201/04 |
| 2001/0023071 A1 | 9/2001 | Sugise | |
| 2008/0249300 A1 | 10/2008 | Herwig | |
| 2016/0031784 A1 | 2/2016 | Micoine | |

FOREIGN PATENT DOCUMENTS

| CN | 1367166 A | 9/2002 |
| CN | 1856459 A | 11/2006 |
| CN | 101432260 A | 5/2009 |
| CN | 105315146 A | 2/2016 |
| EP | 1125909 A1 | 8/2001 |

OTHER PUBLICATIONS

An office action issued on Mar. 23, 2023, for corresponding EP Patent Application.
An office action issued on Oct. 19, 2023 for corresponding Chinese Patent Application.

* cited by examiner

*Primary Examiner* — Golam M Shameem
(74) *Attorney, Agent, or Firm* — Harvest IP Law, LLP

(57) ABSTRACT

The present invention relates to a laurolactam preparation method and synthesis apparatus, and epoxidation and a rearrangement reaction are performed in the conversion of cyclododecene into cyclododecanone so that the preparation method can synthesize laurolactam having a higher purity with a higher selectivity and in a higher yield than a conventional preparation method.

8 Claims, 1 Drawing Sheet

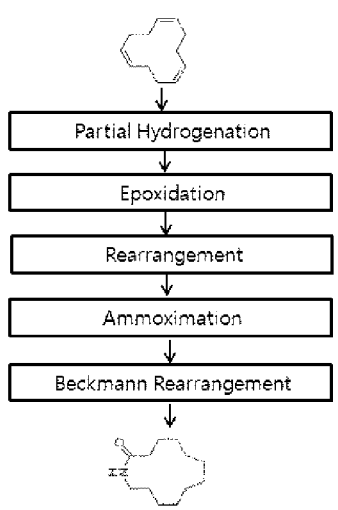

LAUROLACTAM PREPARATION METHOD AND SYNTHESIS APPARATUS

CROSS REFERENCE TO RELATED APPLICATIONS

This is a divisional application of U.S. application Ser. No. 16/343,522 filed Apr. 19, 2019 which is an application of a National Stage of International Application No. PCT/KR2019/017935 filed Dec. 18, 2019, claiming priority based on Korean Patent Application Nos. 10-2018-0165237 filed Dec. 19, 2018

TECHNICAL FIELD

The present invention relates to a novel laurolactam preparation method and apparatus.

BACKGROUND ART

In general, an industrial method of preparing an amide compound is to convert a corresponding oxime compound using a Beckman rearrangement reaction. For example, laurolactam may be synthesized by performing the Beckmann rearrangement reaction on the cyclododecanone oxime. However, a process of the Beckman rearrangement reaction is very complex and uses a concentrated sulfuric acid and a fuming sulfuric acid as catalysts, but these acids are strong acids and require high contents, resulting in a large amount of ammonium sulfate by-product during neutralization. Thus, there is a limitation that a facility for processing such a by-product is required. In addition, the Beckman rearrangement reaction is performed in a solvent, but there is a restriction in selecting the solvent because a solubility of cyclododecanone oxime in the solvent should be high and the solvent should not react with the concentrated sulfuric acid and the fuming sulfuric acid, which are the catalysts.

As a conventional laurolactam preparation method, a "continuous preparation method of laurolactam in a liquid phase" is disclosed in Japanese Patent Laid-Open Publication No. 1977-033118B2. Also in this method, the process of the Beckman rearrangement reaction is performed using a concentrated sulfuric acid as a catalyst, but an by-product of ammonium sulfate is not generated. However, extensive facilities and energy are required for the treatment of waste sulfuric acid, and the remaining cyclododecanone may generate by-products, so it is necessary to complete an oxime reaction to prevent the generation of by-products. In this case, since isopropylcyclohexane used as a solvent is hydrophobic, a movement speed of a substance on an interface between oil and water is slow, and a long time is required for oximation.

Meanwhile, recently, studies on rearrangement catalysts that do not use a large amount of sulfuric acid or fuming sulfuric acid have been actively conducted. Examples of such rearrangement catalysts include a mixed catalyst of an ammonium salt of rhenium peroxide containing a strong acid and a trifluoromethanesulfonic acid, indium triflate, and ytterbium triflate. In addition, there is a method of performing a rearrangement reaction in the presence of a rhenium compound and a nitrogen-containing heterocyclic compound without using an acid. However, even in this case, a catalyst and a solvent used in a preparation method are special, and a recovering and recycling method of the catalyst and the solvent is not clear, such that it is difficult to consider that the method described s completed as an industrial process.

Cyclododecanone oxime for synthesis of laurolactam may be prepared through various synthesis methods. However, these various synthesis methods should include processes having several steps, and studies for finding a more efficient method in constructing the entire process system are thus required.

Specifically, a step of synthesizing cyclododecane by performing a hydrogenation reaction on cyclododecatriene as a first process, and a step of synthesizing cyclododecanone by performing air oxidation on the cyclododecane, followed by hydrolysis and crystallization reactions as a second process, may be considered. However, the above method has a problem that cyclododecene is synthesized in addition the cyclododecane in the first process, such that a third process of separating the cyclododecane and the cyclododecene and re-circulating the cyclododecane to the second process should be accompanied, and cyclododecanol is synthesized in addition to the cyclododecanone in the second process, such that a fourth process of dehydrogenating the cyclododecanol should be accompanied.

DISCLOSURE

Technical Problem

An object of the present invention is to provide a laurolactam preparation method capable of solving a problem that a treatment facility of by-products generated in a large amount while synthesizing high purity cyclododecanone is required, and capable of simplifying an entire process and obtaining laurolactam with high yield and high purity.

Technical Solution

In one general aspect, there is provided a laurolactam preparation method including: a) synthesizing epoxidized epoxidizing cyclododecene cyclododecane by (CDEN) with a catalyst; b) synthesizing cyclododecanone by catalyzing the epoxidized cyclododecane; and c) synthesizing cyclododecanone oxime by performing ammoximation on the cyclododecanone.

Hereinafter, the content to be described later in the Technical Solution section is described as an example and should not be construed as being limited thereto.

The laurolactam preparation method may further include, before the step a), synthesizing cyclododecene (CDEN) by performing a partial hydrogenation reaction on cyclododecatriene (CDT).

The cyclododecatriene (CDT) may be synthesized by performing a cyclotrimerization reaction on 1,3-butadiene with a Ziegler-Natta catalyst.

The partial hydrogenation reaction may be performed through a stirrer in which a negative pressure and a positive pressure are generated by stirring.

The partial hydrogenation reaction may be performed in the presence of a homogeneous catalyst containing ruthenium chloride, triphenyl phosphine, and formaldehyde or carbon monoxide complex.

In the step a), the epoxidation reaction may be performed using a catalyst containing a tungsten oxide salt and a phase transfer agent.

In the step b), an alkali halide may be used as a catalyst.

In the step c), the cyclododecanone oxime may be synthesized by reacting ammonia; hydrogen peroxide; a catalyst containing titanium silicalite; and a reaction activator containing ammonium acetate with the cyclododecanone in a solvent containing ethanol.

The laurolactam preparation method may further include, after the step c), d) synthesizing laurolactam by performing a Beckmann rearrangement reaction on the cyclododecanone oxime.

The Beckman rearrangement reaction may synthesize laurolactam from cyclododecanone oxime through a catalyst containing cyanuric chloride in a solvent containing isopropylcyclohexane.

After the synthesizing of the laurolactam, separating and purifying the laurolactam from a mixture containing the laurolactam may be further included.

In another general aspect, there is provided a laurolactam synthesis apparatus including: a partial hydrogenation reactor in which cyclododecatriene and hydrogen are introduced to synthesize cyclododecene; an epoxidation reactor in which cyclododecene or a mixture containing the cyclododecene and a catalyst are introduced from the partial hydrogenation reactor to synthesize epoxidized cyclododecane; a rearrangement reactor in which an epoxidized cyclododecane or a mixture containing the epoxidized cyclododecane and a catalyst are introduced from the epoxidation reactor to synthesize cyclododecanone; an oximation reactor in which cyclododecanone or a mixture containing the cyclododecanone and ammonia are introduced from the rearrangement reactor to synthesize cyclododecanone oxime; and a Beckman rearrangement reactor in which cyclododecanone oxime or a mixture containing the cyclododecanone oxime is introduced from the oximation reactor to synthesize the laurolactam.

The laurolactam synthesis apparatus may further include a cyclotrimerization reactor in which 1,3-butadien is introduced to synthesize cyclododecatriene and the synthesized cyclododecatriene is introduced into the partial hydrogenation reactor.

In the partial hydrogenation reactor, the cyclododecene may be synthesized by reacting hydrogen; a catalyst containing ruthenium chloride, triphenylphosphine, and formaldehyde; and a catalytically active agent containing any one or more selected from ethanol and acetic acid with the cyclododecatriene in a solvent containing ethanol.

In the epoxidation reactor, the cyclododecene may be reacted by a catalyst containing a tungsten oxide salt and a phase transfer agent.

In the rearrangement reactor, the epoxidized cyclododecane may use an alkali halide as a catalyst to synthesize cyclododecanone.

In the oximation reactor, the cyclododecanone oxime may be synthesized by reacting ammonia; hydrogen peroxide; a catalyst containing titanium silicalite; and a reactive active agent containing ammonium acetate with the cyclododecanone in a solvent containing ethanol.

In the Beckman rearrangement reactor, the laurolactam may be synthesized by reacting a catalyst containing cyanuric chloride with the cyclododecanone oxime in a solvent containing isopropylcyclohexane.

The laurolactam synthesis apparatus may further include a distillation reactor in which laurolactam or a mixture containing the laurolactam is introduced from the Beckman rearrangement t reactor to separate and remove substances other than the laurolactam.

Advantageous Effects

Since the conversion rate and selectivity to a target compound are significantly high in each process from a first reactant to laurolactam, which is a final product, through an intermediate product, a practical industrial process capable of obtaining laurolactam with high yield and high purity may be implemented.

DESCRIPTION OF DRAWINGS

FIG. 1 is a schematic diagram illustrating steps of preparing laurolactam according to the present invention.

BEST MODE

Hereinafter, the present invention will be described in detail. Terms used in the present specification should be interpreted as generally understood by those of ordinary skill in the relevant field, unless otherwise defined. The drawings and embodiments of the present specification are for those of ordinary skill in the art to easily understand and implement the present invention, contents that may obscure the gist of the invention in the drawings and examples may be omitted, and the present invention is not limited to the drawings and examples.

The singular form of terms used in the present invention may be interpreted as including the plural form unless otherwise specified.

The present invention provides a laurolactam preparation method, a laurolactam synthesis apparatus, and a laurolactam preparation system including one or more of the laurolactam preparation method and the laurolactam synthesis apparatus. In the case of performing each process step according to the present invention, an obtained product containing an unreacted remaining material, etc., as well as a target material synthesized in each step may be used as a reactant in a next step as it is without being separated by a separate process, and an effect that a conversion rate and selectivity are significantly high up to a final step of synthesizing laurolactam is implemented.

The laurolactam preparation method according to the present invention includes: a) synthesizing epoxidized cyclododecane by epoxidizing cyclododecene (CDEN) with a catalyst; b) synthesizing cyclododecanone by catalyzing the epoxidized cyclododecane; and c) synthesizing cyclododecanone oxime by performing ammoximation on the cyclododecanone.

There may be a method of performing air oxidation from cyclododecene (CDEN) directly to cyclododecanone (CDON) without undergoing an epoxidation process as the present invention. However, in this case, the yield of laurolactam, which is the final product, is significantly reduced because the yield is 20% or less which is very low. However, when the epoxidized cyclododecane is produced through an epoxidation process and then converted to cyclododecanone through a rearrangement reaction using a catalyst, it is possible to achieve an effect that cyclododecanone is obtained in a yield of 95% or more.

The present provides invention a laurolactam preparation method further including, before the step a), synthesizing cyclododecene (CDEN) by performing a partial hydrogenation reaction on cyclododecatriene (CDT).

As mentioned above, in a case of the conventional method of synthesizing cyclododecane from which all double bonds have been removed by performing a hydrogenation reaction on cyclododecatriene (CDT), and synthesizing cyclododecanone by performing an air oxidation reaction on cyclododecane, followed by hydrolysis and crystallization, there is an inconvenience of using a method of separately separating by-products that may be synthesized together in the process and performing circulation through an additional process, and in this process, a conversion rate of a reactant and selectivity of a required compound are significantly reduced.

However, in the case of performing the above-described steps a) and b), after performing a partial hydrogenation reaction of cyclododecatriene (CDT), before the step a), the entire process is significantly simplified and a conversion rate of reactant and selectivity of laurolactam may be significantly improved, compared to the conventional method.

The cyclododecatriene (CDT) may be synthesized through various pathways. As a preferred example, the cyclododecatriene (CDT) may be synthesized by performing a cyclotrimerization reaction on 1,3-butadiene with a Ziegler-Natta catalyst. In the case of performing the partial hydrogenation reaction on the mixture obtained with cyclododecatriene synthesized by such a method, selectivity of laurolactam, which is the final product, and a conversion rate may be significantly improved. However, this is a preferred example, and cyclododecatriene may be synthesized through other routes, such that the present invention is not limited thereto.

The partial hydrogenation reaction may be performed through a stirrer in which a negative pressure and a positive pressure are generated by stirring. The negative pressure is generated by the stirring to bring a gas-phase hydrogen having a positive pressure into contact with a liquid-phase cyclododecatriene, such that forced dispersion is made, and the dispersion efficiency may be increased by increasing a stirring speed. In addition, when a stirrer in which the positive and negative pressures are generated is used, it is possible to obtain a product having high yield and excellent selectivity without taking the following measure such as separating reactors step by step or adding a solvent such as acetic acid or ethanol.

However, this is only described as a preferred example, and the present invention may use a variety of known partial hydrogenation reaction methods, and should not be construed as being limited thereto.

The catalyst used in the partial hydrogenation reaction is not limited as long as it allows hydrogen to be partially added to cyclododecatriene, and the partial hydrogenation reaction may be preferably performed in the presence of a homogeneous catalyst containing ruthenium chloride, triphenyl phosphine (TPP), formaldehyde or carbon monoxide complex.

Triphenylphosphine (TPP) forms a complex with ruthenium chloride to act as a catalyst for partial hydrogenation reaction, and in this case, acetic acid or ethanol may be further used as a catalytically active agent to further activate the reaction of the catalyst. Therefore, the conversion rate into cyclododecene (CDEN) including one double bond and selectivity thereof may be significantly improved. However, this is merely a preferred example, and the present invention is not limited thereto.

An amount of hydrogen supplied in the partial hydrogenation reaction is not limited as long as hydrogen is continuously supplied so that cyclododecatriene may sufficiently react with hydrogen, and one example is that hydrogen is supplied by controlling a flow rate so that a total reaction pressure is preferably maintained at 10 to 80 bar, and more preferably 20 to 40 bar. However, this is merely a preferred example, and the present invention is not limited thereto.

The content of the catalyst used in the partial hydrogenation reaction is not limited as long as hydrogen may be partially added to cyclododecatriene. Preferably, the catalyst may be used in an amount of 0.1 to 15 parts by weight based on 100 parts by weight of cyclododecatriene, and specifically, ruthenium chloride in the catalyst may be used in an amount of 0.0001 to 1 part by weight, triphenylphosphine in the catalysts may be used in an amount of 0.1 to 10 parts by weight, and formaldehyde may be used in an amount of 0.3 to 3 parts by weight.

In addition, a catalytically active agent may be sufficient as long as hydrogen may further activate the partial hydrogenation reaction of cyclododecatrien. Preferably, the catalytically active agent may be used in an amount of 0.1 to 3 parts by weight based on 100 parts by weight of cyclododecatriene, and specifically, as a catalytically active agent, acetic acid may be used in an amount of 0.01 to 2 parts by weight, and ethanol may be used in an amount of 0.1 to 3 parts by weight. However, this is merely a preferred example, and the present invention is not limited thereto.

The selectivity for the material synthesized by the partial hydrogenation reaction and the conversion rate of the raw material for the synthesis may be 95 to 99.9%, more preferably 98 to 99.9%.

In the laurolactam preparation method according to the present invention, in the step a), the epoxidation reaction may be performed using a catalyst containing a tungsten oxide salt and a phase transfer agent. Oxidation proceeds by receiving oxygen from hydrogen peroxide present in a receiving layer through a phase transfer catalyst and transferring the oxygen to cyclododecene present in an organic layer.

In the case of the tungsten oxide salt, tungstic acid ($H_2WO_4$) may be any one selected from the group consisting of ammonium tungstate, sodium tungstate, and lithium tungstate, preferably tungstic acid. However, this is merely a preferred example, and the present invention is not limited thereto. The phase transfer catalyst is not limited as long as it contributes to material transfer between an aqueous layer and an organic layer, and may preferably include trioctylamine.

The content of the catalyst used in the epoxidation reaction is not limited as long as epoxidation occurs from cyclododecene, but may be preferably 0.002 to 10 parts by weight based on 100 parts by weight of cyclododecene, and specifically, the content of tungsten oxide salt may be 0.001 to 10 parts by weight, and the content of phase transfer catalyst may be 0.001 to 10 parts by weight. However, this is merely a preferred example, and the present invention is not limited thereto.

The epoxidized cyclododecane synthesized by the epoxidation reaction may have a conversion rate from cyclododecene of 95 to 99.9%, more preferably 98 to 99.9%.

In the laurolactam preparation method according to the present invention, in the step b), a catalyst may be alkali halide, and preferably lithium halide. More preferably, lithium bromide may be used as the catalyst. However, this is an example of the present invention, and the catalyst is not limited thereto. The epoxide is rearranged as a ketone functional group by using the alkali halide as the catalyst.

The content of the alkali halide catalyst used is not limited as long as a rearrangement reaction occurs from the epoxidized cyclododecane to form a ketone functional group, but may be preferably 0.01 to 10 parts by weight based on 100 parts by weight of the epoxidized cyclododecane. However, this is only a preferred example, and the present invention is not limited thereto.

In the laurolactam preparation method according to the present invention, the step c) may be a step of synthesizing cyclododecanone oxime by reacting ammonia; hydrogen peroxide; a catalyst containing titanium silicalite; and a reaction activator containing ammonium acetate with cyclododecanone in a solvent containing ethanol.

The content of ethanol used is not limited as long as the cyclododecanone is sufficiently dissolved to perform an oximation reaction. Preferably, ammonia may be used so that the total pressure is 1.3 to 2.5 bar, and hydrogen peroxide may be used at 0.5 to 3.5 mL/min for 10 to 40 minutes. However, this is only a preferred example and the present invention is not limited thereto.

As a catalyst for inducing the oximation reaction, various known compounds may be used, preferably, for example, titanium silicalite. The content of the catalyst used is not limited as long as the oximation reaction may be performed, and may be specifically 1 to 80 parts by weight based on 100 parts by weight of cyclododecanone. However, this is only a preferred example, and the present invention is not limited thereto.

For the oximation reaction, a reaction active agent may be further used, preferably, for example, ammonium acetate. The content of the reaction active agent used may be sufficient as long as the oximation reaction may proceed, and specifically, may be 3 to 30 parts by weight based on 100 parts by weight of cyclododecanone. However, this is only a preferred example, and the present invention is not limited thereto.

A reaction temperature and a reaction time in the oxime reaction may be sufficient as long as the cyclododecanone is capable of oxime reaction, and specifically, for example, 50 to 100° C. and 15 to 70 minutes. However, this is only a preferred example, and the present invention is not limited thereto.

The present invention provides a method for producing laurolactam further including, after the step c), d) synthesizing laurolactam by performing a Beckmann rearrangement reaction on the cyclododecanone oxime.

In the step d), various catalysts may be used to proceed the Beckman rearrangement reaction. A catalyst containing cyanuric chloride, etc., is preferable, and zinc chloride, etc., is preferably used together with the above catalyst, as a cocatalyst. The contents of cyanuric chloride and zinc chloride used are not limited as long as the Beckman rearrangement reaction may be performed on the cyclododecanone oxime and may be specifically, for example, 0.001 to 0.1 parts by weight, respectively, based on 100 parts by weight of cyclododecanone oxime. However, this is only a preferred example and the present invention is not limited thereto.

In the step d), the solvent is not limited as long as the Beckman rearrangement reaction may be performed on the cyclododecanone oxime, and may be preferably, for example, isopropylcyclohexane. The content of the solvent used is not limited as long as laurolactam may be synthesized by performing the Beckman rearrangement reaction on the cyclododecanone oxime.

In the step d), the reaction temperature and the reaction time are not limited as long as the cyclododecanone oxime is subjected to the Beckman rearrangement reaction, preferably, for example, 70 to 130° C. and 1 to 20 minutes, respectively. However, this is only a preferred example and the present invention is not limited thereto.

Since the product obtained in the step d) may contain a solvent and an unreacted residual material, etc., in addition to laurolactam, which is a target substance, it is preferable to perform the step of separating and purifying the laurolactam from such a mixture.

Thus, the laurolactam preparation method according to the present invention may further include, after step d), e) separating and purifying the laurolactam from a mixture containing the laurolactam. Here, the method of separating and purifying the laurolactam may use various known methods.

The selectivity for the material synthesized in the step d) and the conversion rate of the raw material for the synthesis, may be 95 to 99.9%, more preferably 98 to 99.9%.

In addition, the present invention may provide a laurolactam synthesis apparatus according to the laurolactam preparation method described above. In this case, since the contents mentioned in the laurolactam preparation method correspond to substantially the same technical idea, the materials used, reaction conditions, etc., should be interpreted substantially the same as those described above.

A laurolactam synthesis apparatus according to the present invention may includes: a partial hydrogenation reactor in which cyclododecatriene and hydrogen are introduced to synthesize cyclododecene; an epoxidation reactor in which cyclododecene or a mixture containing the cyclododecene and a catalyst are introduced from the partial hydrogenation reactor to synthesize epoxidized cyclododecane; a rearrangement reactor in which an epoxidized cyclododecane or a mixture containing the epoxidized cyclododecane and a catalyst are introduced from the epoxidation reactor to synthesize cyclododecanone; an oximation reactor in which cyclododecanone or a mixture containing the cyclododecanone and ammonia are introduced from the rearrangement reactor to synthesize cyclododecanone oxime; and a Beckman rearrangement reactor in which cyclododecanone oxime or a mixture containing the cyclododecanone oxime is introduced from e oximation reactor to synthesize the laurolactam.

The laurolactam synthesis apparatus according to an exemplary embodiment of the present invention may further include a cyclotrimerization reactor in which 1,3-butadien is introduced to synthesize cyclododecatriene and the synthesized cyclododecatriene is introduced into the partial hydrogenation reactor.

In an exemplary embodiment of the present invention, in the partial hydrogenation reactorj, the cyclododecene may be synthesized by reacting hydrogen; a catalyst containing ruthenium chloride, triphenylphosphine, formaldehyde or carbon monoxide complex; and a catalytically active agent containing acetic acid or ethanol with cyclododecatriene in a solvent containing ethanol.

In an exemplary embodiment of the present invention, in the epoxidation reactor, the cyclododecene may be reacted by a catalyst containing a tungsten oxide salt and a phase transfer agent.

In addition, in the rearrangement reactor, the epoxidized cyclododecane may use an alkali halide as a catalyst to synthesize cyclododecanone.

In an exemplary embodiment of the present invention, in the oximation reactor, the cyclododecanone oxime may be synthesized by reacting ammonia; hydrogen peroxide; a catalyst containing titanium silicalite; and a reactive active agent containing ammonium acetate with the cyclododecanone in a solvent containing ethanol.

In an exemplary embodiment of the present invention, in the Beckman rearrangement reactor, the laurolactam may be synthesized by reacting a catalyst containing cyanuric chloride with the cyclododecanone oxime in a solvent containing isopropylcyclohexane.

According to an exemplary embodiment of the present invention, the laurolactam synthesis apparatus may further include a distillation reactor in which laurolactam or a mixture containing the laurolactam is introduced from the Beckman rearrangement reactor to separate and remove substances other than the laurolactam.

As a "reactor" mentioned in the present invention, various known reactors may be used, and a specification and a size thereof are not limited because they may be appropriately adjusted according to a scale and environment of a process. In addition, each reactor may be provided with various inlet pipes, outlet pipes, etc., for introducing or discharging substances thereinto or therefrom, and the use of various apparatuses for adjusting amounts of substances introduced into or discharged from each reactor and various apparatuses for controlling these various apparatuses may be appropriately adjusted by those skilled in the art.

Hereinafter, the present invention will be described in detail through examples, but the examples are for the purpose of describing the present invention in more detail, and the scope of the present invention is not limited by the following examples.

Example 1

Cyclododecene Synthesis Process 200 g of cyclododecatriene (CDT), 40 mg of $RuCl_3$, 5.56 g of triphenylphosphine (TPP) (110:1=TPP:Ru), 3.44 g of 35% formalin (TPP:formalin=1:2), 0.5 g of acetic acid, and 10.54 g of ethanol were added to a high-speed stirring batch reactor (500 ml, 800 rpm), and the reactor was connected. Then, the reactor was purged 3 times with 5 kg/cm$^2$ of nitrogen ($N_2$) and 3 times with hydrogen gas ($H_2$), and then the reactor pressure was filled to 10 barg. Then, the temperature of the reactor was raised from 25° C. to 145° C. for about 40 minutes, and when the pressure of the reactor started to drop, the pressure of the reactor was raised to 20 bar, and the temperature was raised to 160° C. for about 10 minutes, and this was maintained during the reaction. The reaction was performed a total of 6 hours, and in this case, hydrogen was continuously supplied in order to maintain the pressure continuously. After the reaction was completed, the conversion rate of final cyclododecatriene was 98.2% and the selectivity of cyclododecene was 98.5%.

Epoxidized Cyclododecane Synthesis Process 25 g of cyclododecene, 0.075 g of tungstic acid ($H_2WO_4$), 0.06 g of $H_3PO_4$, 0.105 g of tri-n-octyl amine, 1.4 g of $H_2O$, 1.02 g of 50% $H_2O_2$ were added to a high-speed stirring batch reactor (100 mL). The reaction was performed at 100° C. for a total of 4 hours, and 85 ul/min of hydrogen peroxide was injected through a pump while stirring the contents of the reactor at 1500 rpm during the reaction. After the reaction was completed, the conversion rate of final cyclododecene was 98% and the selectivity of epoxidized cyclododecane was 99%.

Cyclododecanone Synthesis Process 5 g of epoxidized cyclododecane and 0.085 g of lithium bromide (LiBr) were added in a 50 mL round flask under inert condition using a glovebox. Then, after making a nitrogen balloon and connecting the nitrogen balloon to the flask, the flask was added in an oil bath containing silicone oil and stirred while heating to 200° C. The time taken to complete the reaction was 120 minutes, and after the reaction was completed, the conversion rate to cyclododecanone was 99% or more, and the selectivity thereof was 95% or more.

Cyclododecanone Oxime Synthesis Process 73 g of the mixture (including cyclododecanone) finally obtained in the above cyclododecanone synthesis process, 535 g of ethanol, 8.5 g of ammonium acetate, and 30 g of a titanium silicalite (TS-1) catalyst powder were added in a pressure reactor (2 L) equipped with a stirrer, and the mixture was heated to 80° C. Then, $NH_3$ gas (ammonia gas) was injected until the reactor became 1.8 barg, and stirred at 500 rpm for 30 minutes so that $NH_3$ could be easily dissolved in the solution. Subsequently, a 30% by weight of aqueous hydrogen peroxide solution was injected while stirring at a flow rate of 2.45 mL/min.

The reaction completion time was 25 minutes, the conversion rate of cyclododecanone was 99% or more, the selectivity of cyclododecanone oxime was 99% or more, and the reaction rate of hydrogen peroxide was 78%.

Laurolactam Synthesis Process 3 g of the mixture (cyclododecanone oxime) obtained in the cyclododecanone synthesis process, 12 g of isopropylcyclohexane, 0.045 g of cyanuric chloride, and 0.03 g of zinc chloride were added in a 100 mL round flask. In addition, the temperature was adjusted to 95° C. using a heating mantle, and the reaction was performed by stirring at 200 rpm or more. The reaction completion time was 5 minutes, the conversion rate of cyclododecanone oxime was 99% or more, and the selectivity of laurolactam was 99% or more.

Example 1 shows that even though the mixture containing a compound obtained in each step was used as a reactant in the next step as it is, both the conversion rate of the reactant and the selectivity of laurolactam, which is the target compound, were 998 or more. It can be seen that the process efficiency is very excellent because it was confirmed that both the conversion rate and the selectivity were 998 or more, although the process is simplified compared to the conventional method.

The invention claimed is:

1. A laurolactam synthesis apparatus, comprising:
a partial hydrogenation reactor in which cyclododecatriene and hydrogen are introduced to synthesize cyclododecene;
an epoxidation reactor in which cyclododecene or a mixture containing the cyclododecene and a catalyst are introduced from the partial hydrogenation reactor to synthesize epoxidized cyclododecane;
a rearrangement reactor in which an epoxidized cyclododecane or a mixture containing the epoxidized cyclododecane and a catalyst are introduced from the epoxidation reactor to synthesize cyclododecanone;
an oximation reactor in which cyclododecanone or a mixture containing the cyclododecanone and ammonia are introduced from the rearrangement reactor to synthesize cyclododecanone oxime; and
a Beckman rearrangement reactor in which cyclododecanone oxime or a mixture containing the cyclododecanone oxime is introduced from the oximation reactor to synthesize the laurolactam.

2. The laurolactam synthesis apparatus of claim 1, further comprising: a cyclotrimerization reactor in which 1,3-butadien is introduced to synthesize cyclododecatriene and the synthesized cyclododecatriene is introduced into the partial hydrogenation reactor.

3. The laurolactam synthesis apparatus of claim 1, wherein in the partial hydrogenation reactor, the cyclododecene is synthesized by reacting hydrogen; a catalyst containing ruthenium chloride, triphenylphosphine, formaldehyde or carbon monoxide complex; and a catalytically active agent containing acetic acid or ethanol with cyclododecatriene in a solvent containing ethanol.

4. The laurolactam synthesis apparatus of claim 1, wherein in the epoxidation reactor, the cyclododecene is reacted by a catalyst containing a tungsten oxide salt and a phase transfer agent.

5. The laurolactam synthesis apparatus of claim 1, wherein in the rearrangement reactor, the epoxidized cyclododecane uses an alkali halide as a catalyst to synthesize cyclododecanone.

6. The laurolactam synthesis apparatus of claim 1, wherein in the oximation reactor, the cyclododecanone oxime is synthesized by reacting ammonia; hydrogen peroxide; a catalyst containing titanium silicalite; and a reactive active agent containing ammonium acetate with the cyclododecanone in a solvent containing ethanol.

7. The laurolactam synthesis apparatus of claim 1 wherein in the Beckman rearrangement reactor, the laurolactam is synthesized by reacting a catalyst containing cyanuric chloride with the cyclododecanone oxime in a solvent containing isopropylcyclohexane.

8. The laurolactam synthesis apparatus of claim 1, further comprising a distillation reactor in which laurolactam or a mixture containing the laurolactam is introduced from the Beckman rearrangement reactor to separate and remove substances other than the laurolactam.

* * * * *